METHOD FOR ATTACHING SUTURE NEEDLE

Original Filed Aug. 25, 1969 2 Sheets-Sheet 1

INVENTORS
WILLIAM H. SHAVE
LEONARD D. KURTZ
BY Larson and Taylor
ATTORNEYS

METHOD FOR ATTACHING SUTURE NEEDLE

Original Filed Aug. 25, 1969 2 Sheets-Sheet 2

INVENTORS
WILLIAM H. SHAVE
LEONARD D. KURTZ
BY Larson and Taylor
ATTORNEYS

United States Patent Office

Re. 27,735
Reissued Aug. 14, 1973

27,735

METHOD FOR ATTACHING SUTURE NEEDLE

William H. Shave, Roosevelt, Long Island, and Leonard D. Kurtz, Woodmere, N.Y., assignors to Deknatel, Incorporated, Queens Village, N.Y.

Original No. 3,611,551, dated Oct. 12, 1971, Ser. No. 852,785, Aug. 25, 1969. Application for reissue Aug. 29, 1972, Ser. No. 284,543
Int. Cl. B21d *39/00;* B23p *11/00*
U.S. Cl. 29—515 6 Claims

Matter enclosed in heavy brackets [ ] appears in the original patent but forms no part of this reissue specification; matter printed in italics indicates the additions made by reissue.

ABSTRACT OF THE DISCLOSURE

A method of attaching a suture to a suture needle of the type initially having a V-shaped cross-section channel while substantially eliminating annealing. The channel is forcefully partially closed before hardening the needle, after which the needle is hardened, after which suture is placed into the channel. The walls of the channel are then further and finally closed against each other normally without annealing, to hold the suture.

BACKGROUND OF THE INVENTION

This invention relates to suture needles, and in particular, it relates to the attachment of a suture to a suture needle.

Suture needles are formed from a relatively soft metal wire-like material. A length of wire of sufficient length for both the needle and a handle (for holding the needle during the manufacture thereof) is cut from the main wire source. The length is then straightened, formed with a point at the front end, and a part of the shank to the rear of the point may be flattened to provide a place for the surgeon to grip the needle.

When using the channel method for attaching the suture to the needle, a channel is formed in the needle, rearward of the shank while the needle is still in its initial, relatively soft condition. This groove is stamped into the needle by means of a V-shaped die. The V-shape of the die is necessary to assure that a sufficient force is concentrated at the appropriate place on the channel to form a groove of a sufficient depth without damaging the walls of the newly formed channel.

The needle point is now bent to the desired curvature and the needle is hardened. This may be accomplished by placing the needles into a vacuum furnace at approximately 1800° F. to 1900° F. followed by tempering at about 500° F. to take out the brittleness. The finished needle may have a Rockwell hardness of approximately 49 to 55.

Since the suture could not withstand the heat treatments, it must of course be attached to the needle after hardening. However, it is impossible to bend the hardened channel walls to close them onto a suture without cracking or twisting the walls. Thus, before closing the channel walls onto suture it is necessary to soften the channel walls by annealing. Of course, care must be taken to prevent the softening effect of the annealing procedure from being felt forward of the channel walls along the shank or the needle point.

Following annealing the needle is electroplated, and the handle part is chopped off leaving the channel open to the rear. The suture is then inserted and the channel walls are closed onto the suture, preferably by crimping to hold the suture.

Notwithstanding the necessity of the annealing procedure, it has been found that annealing has several detrimental effects. First, there is an inevitable drift of heat down the shank of the needle causing some undesirable annealing effect on the shank of the needle itself. In addition, the annealing process invariably decreases the "stainlessness" of the needle, that is the ability of the needle to resist rust.

Further, the "chop off" of the handle from the main part of the needle is less clean with a softer annealed needle than with a harder needle. This "chop off" is accomplished through that portion of the needle which has the channel formed into it. The harder the material of the channel, the cleaner the chop off, and the smaller the resultant burr. The annealing process by softening the channel prevents a clean chop off and makes it more likely for burrs to occur.

Moreover, the above disadvantages can become even more significant when the needle is treated to obtain a very high Rockwell hardness. In this case it may be necessary to anneal the needle several times, thereby significantly increasing the above noted undersirable effects.

Indeed, with a very hard needle, it is frequently impossible or difficult to accomplish the necessary softness for bending the needle material without cracking or twisting the same regardless of the number of annealing steps.

Thus, there exists a need for improvements which will permit the use of the advantageous channel method of attaching the suture to the needle while concurrently eliminating the disadvantages which result from annealing.

SUMMARY OF THE INVENTION

Thus, it is a purpose of the invention to provide a new and improved method for attaching a suture to a suture needle by the channel method while eliminating the detrimental effects of annealing.

The purpose of the present invention is achieved by partially closing the V-shaped groove while the needle is still in its initial relatively soft condition before the hardening step. Because of this "preclosing" step, it is possible to later close the channel of the hardened needle without annealing, or at worst (in the case of very hard needles) by substantially reducing the required number of annealing steps.

A preferred embodiment of the invention is as follows: First, while the length of needle wire still has its initial softness, the needle point and the V-shaped channel are formed in the conventional manner. The said V-shaped channel is stamped out by applying a V-shaped die against the wire. Next, and before hardening takes place, the walls of the channel are partially closed. The extent of this closing will depend upon specific operating conditions. As a lower limit, the channel should be closed enough so that after subsequent hardening and the insertion of the suture, further and final closing will not cause the channel walls to crack or twist. As an upper limit, the channel opening should be left wide enough to permit insertion of the suture into the channel. In this condition the channel walls may still diverge, although of course less than the initial V-shape. Or the channel walls may be parallel to each other or they may even converge towards each other. The needle is then hardened in a conventional manner, for example by heating in a vacuum furnace at 1800–1900° F. followed by tempering at about 500° F. to remove brittleness. The suture end is then placed into the partially closed, hardened channel after which the channel is finally closed onto the suture to hold the same without annealing (or if working with a very hard needle, with a substantially reduced number of annealings) and also without cracking or twisting the walls of the channel and without otherwise compromising the structural integrity of the channel walls or of the needle as a whole.

For example, we have been able to close without cracking or twisting the channels of hard needles up to 0.040 inch in diameter without annealing. Needles of 0.060 inch in diameter, previously requiring from three to eight annealings were closed successfully with only one annealing.

In addition, since there is no annealing, there is no drift of heat down the shank to cause an annealing effect on the shank of the needle. The needle is now uniformly hard along its length and it is possible to place the needle holder at any position along the length of the needle. The resistance to bending is now as high as possible since the needle is as hard as possible, without brittleness. This is in contrast with annealed needles of the prior art wherein the surgeon had to be careful in the placement of the needle holder on the needle to be use that he did not grasp a spot which had become soft from the annealing.

Another advantage of the present invention is that the stainlessness, that is the ability of the needle to resist rust is maintained.

Another advantage of the present invention is that the tendency for burr formation at the chop off is greatly decreased or eliminated.

Another advantage of the present invention is that the time of the final closing procedure is significantly reduced. Without the preclosure step, it was frequently found that the hardened needle channel had to be closed gradually in steps. This procedure has been eliminated, however, by using the preclosing step. It is now possible to close the hardened channel in one single step or at most two. Moreover, it has been found that the holding power of this channel is not reduced by the process of the present invention. The final closing procedure is further enhanced since the operator requires less skill to finally close the previously preclosed channel onto the suture. With previous procedures, there was a tendency for the needle to twist as the walls were closed. However, with the preclosed needle the tendency for twisting is completely eliminated. Finally, the symmetry of the closure has been enhanced by the preclosing step.

Thus, it is an object of this invention to provide a new and improved method for attaching a suture to a suture needle.

It is another object of this invention to provide a new and improved method for attaching a suture to a suture needle by the channel procedure wherein the need for annealing is substantially reduced and/or eliminated.

It is another object of this invention to preclose the channel of a suture needle prior to hardening thereof.

Another object of this invention is to provide a new and improved method for attaching a suture to a suture needle of the type having a channel formed in the end thereof remote from the needle point, the method including preclosing the channel of the conventional needle before hardening the needle, and then hardening the needle, inserting the suture into the channel, and closing the channel about the suture.

Other objects and the attendant advantages of the present invention will become apparent from a detailed description to follow together with the accompanying drawings.

BRIEF DESCRIPTION OF THE DRAWINGS

There follows a detailed description of a preferred embodiment of the invention to be read together with the accompanying drawings. However, it is to be understood that both the description and the drawings are provided only to describe a preferred embodiment of the invention, and that the invention is capable of numerous further modifications and variations.

DETAILED DESCRIPTION OF THE PREFERRED EMBODIMENT

Figure 1:
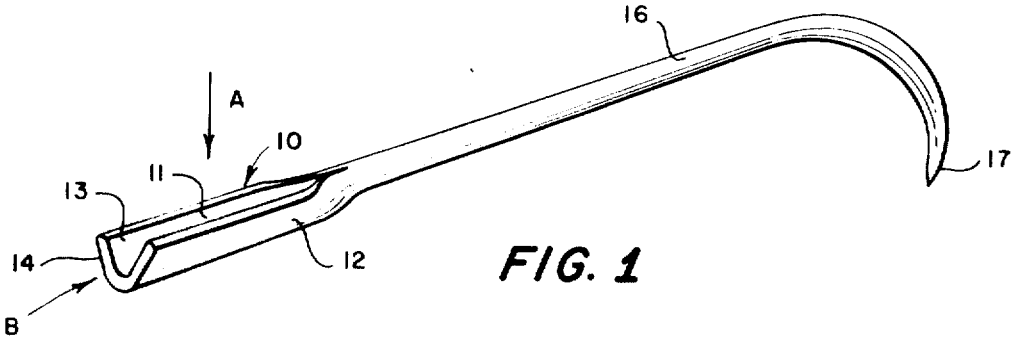
FIG. 1 is a perspective view of a conventional suture needle having a conventional stamped V-shaped channel formed in the end thereof.

Referring now to the drawings, like numerals represent like elements throughout the several views.

Figure 2:
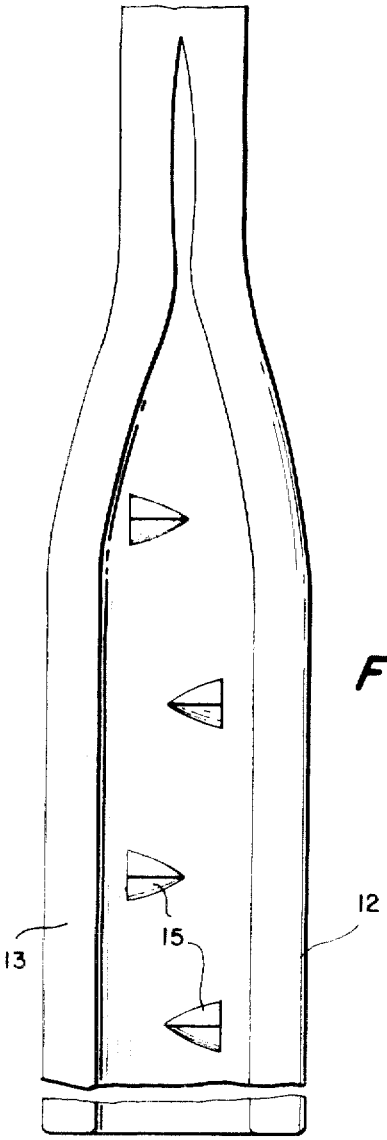
FIG. 2 is a plan view taken in the direction of the arrow A of FIG. 1.
Figure 3:
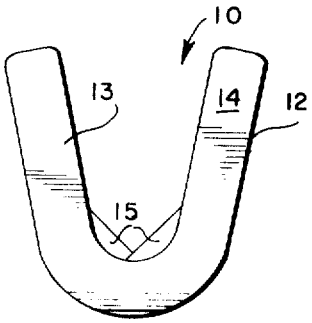
FIG. 3 is an end elevational view taken in the direction of the arrow B in FIG. 1.

FIGS. 1 through 3 illustrate a conventional suture with the needle point formed at the front end and with a V-shaped channel 11 having walls 12 and 13 stamped into the rear end, the needle being ready for further treatment. The additional portion of wire normally used as a handle and chopped off just prior to the insertion of the suture is omitted for purposes of clarity. For holding the suture in place, the channel includes nibs 15. A shank 16 extends from the channel 11 to the point 17.

Normally the needle as illustrated in FIGS. 1 through 3 would now be hardened, and then the channel would be annealed a sufficient number of times, depending upon the exact composition of the material of the needle and upon the size of the channel. After the channel had reached a sufficient softness, the suture end would be placed in the stamped out V-shaped channel 11 and the walls 12 and 13 would be closed about the suture to firmly hold the same. However, as noted earlier, annealing causes several undesirable effects.

Figure 4:
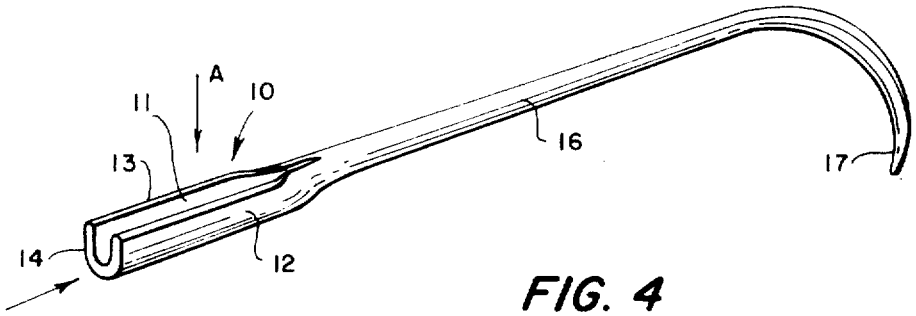
FIG. 4 is a perspective view similar to FIG. 1 but showing the suture needle after the preclosing step.
Figure 5:
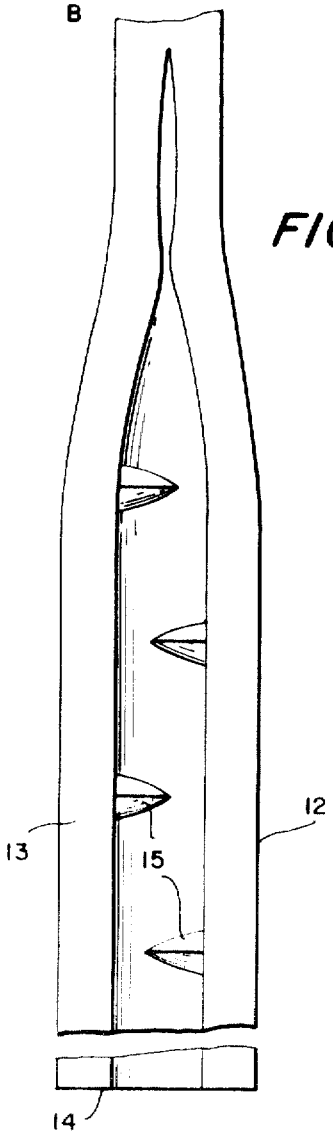
FIG. 5 is a plan view taken in the direction of the arrow A in FIG. 4.
Figure 6:
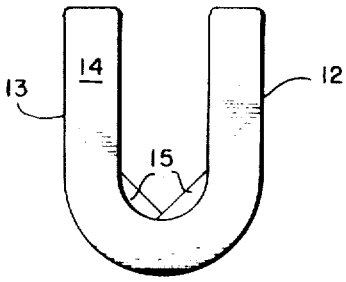
FIG. 6 is an end elevational view taken in the direction of the arrow B in FIG. 4.

FIGS. 4 through 6 illustrate the same needle as FIGS. 1 through 3 but after a preclosing operation has been performed. It can be seen that the walls 12 and 13 are now closer together than in FIGS. 1–3. It has been found that by first bending the needle channel into this shape before hardening the needle wire, then after hardening the walls 12 and 13 could be bent onto a suture normally without annealing, by crimping or the like to firmly hold the suture without causing cracks or twisting of the metal channel walls. Actually, in practice for large needles wherein a large number of annealings have been required, with the present invention only a single annealing was necessary. However, it is believed that even this single annealing could possibly be eliminated.

Figure 7:
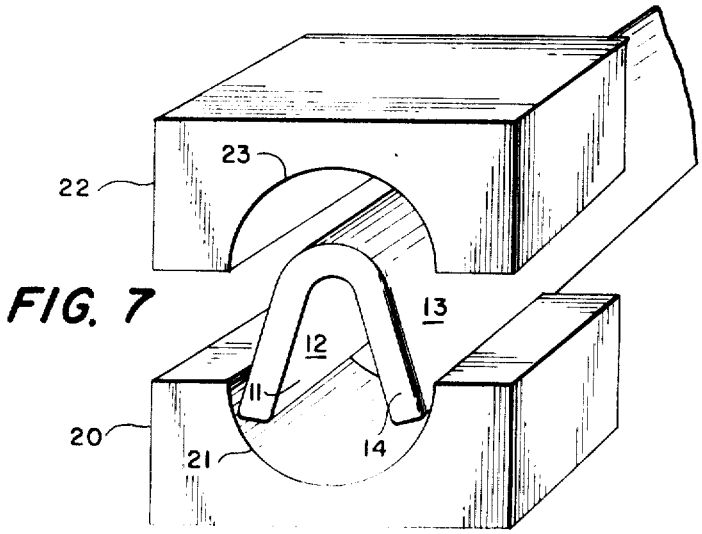
FIGS. 7 and 8 show one arrangement for carrying out the preclosing operation of the present invention.
Figure 8:
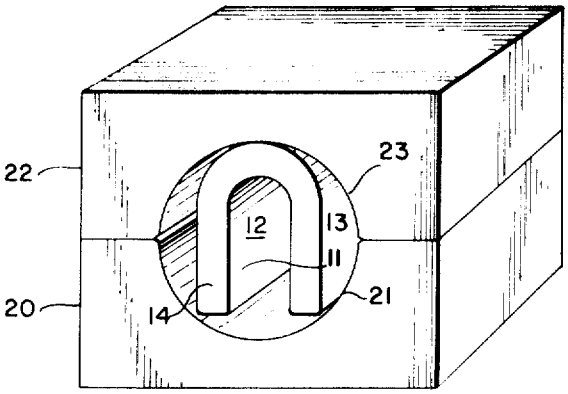

FIGS. 7 and 8 illustrate the tools for carrying out the preclosing step. These include first and second opposed dies 20 and 22 having opposed cylindrical recesses 21 and 23 formed therein. As can be seen by observing FIGS. 7 and 8, the radius of the cylindrical recesses 21 and 23 is such that when the parts 20 and 22 are brought together the outer ends of walls 12 and 13 are forced together for example, into the U shape as shown in FIG. 8.

Although the invention has been described in considerable detail with respect to a preferred embodiment thereof, it will be apparent that the invention is capable of numerous modifications and variations, apparent to those skilled in the art without departing from the spirit and scope of the invention.

We claim:

1. A method of attaching a suture to a suture needle comprising the steps of: [heating] *taking* a metallic suture needle *of soft metal wire-like material* [to soften it], and while the needle is still *in its* [hot and] soft *condition* [and without annealing at this time], (a) flattening a portion of the needle remote from the point, (b) forming said flattened part into a generally V-shaped channel in which the side walls of the channel diverge away from each other, and (c) partially preclosing the V-shaped channel by bringing the walls of the channel closer to each other; hardening the partially closed suture needle, locating a suture in said partially closed channel, and subsequently forcing the walls of the channel closer together to hold the suture in the channel.

2. The method of claim 1, wherein said preclosing step is performed by placing the said channel, while still of V shaped cross-section, into a die comprising a pair of opposed semi-cylindrical recesses, such that the axes of the recesses are parallel to the axis of the channel, and urging the dies together such that the walls of the channel are bent towards each other.

3. The method of claim 1, wherein the step of attaching the suture to the needle is performed without annealing the needle.

4. The method of claim 1, wherein after hardening, the suture is placed into the channel and the walls of the channel are closed onto the suture in the absence of annealing and without cracking the channel walls.

5. The method of claim 1, wherein the further closing is performed while retaining the structural integrity of the channel walls by preventing cracking or twisting thereof.

6. The method of claim 1, wherein after hardening the needle has a Rockwell hardness of between 49 and 55.

References Cited

The following references, cited by the Examiner, are of record in the patented file of this patent or the original patent.

UNITED STATES PATENTS

| | | | |
|---|---|---|---|
| 1,250,114 | 12/1917 | Bigelow et al. | 128—339 |
| 1,441,459 | 1/1923 | Small | 29—517 X |
| 1,636,615 | 7/1927 | Quint | 163—5 X |
| 2,534,867 | 12/1950 | Hennessey | 29—517 X |
| 2,620,028 | 12/1952 | Kohut | 128—339 X |
| 2,865,375 | 12/1958 | Banks et al. | 128—339 |
| 2,865,376 | 12/1958 | Pellier et al. | 128—339 |

CHARLIE T. MOON, Primary Examiner

U.S. Cl. X.R.

128—339; 163—5